United States Patent [19]

Meissner et al.

[11] Patent Number: 5,045,135
[45] Date of Patent: Sep. 3, 1991

[54] APPARATUS AND METHOD FOR CUTOFF REGISTER CONTROL FOR DIAPER MACHINES

[75] Inventors: George H. Meissner; Bart C. Hardy; Timothy M. LeRoy, all of Green Bay, Wis.

[73] Assignee: Paper Converting Machine Company, Green Bay, Wis.

[21] Appl. No.: 614,393

[22] Filed: Nov. 15, 1990

[51] Int. Cl.$^5$ .............................................. B32B 31/00
[52] U.S. Cl. ...................................... 156/64; 156/351; 382/8; 382/48
[58] Field of Search ....................... 156/351, 353, 64; 250/548, 557, 561, 571, 559; 382/8, 48

[56] References Cited

U.S. PATENT DOCUMENTS

| | | | |
|---|---|---|---|
| 3,761,177 | 9/1973 | Corse | 250/548 |
| 3,919,561 | 11/1975 | Coberly | 250/561 |
| 4,325,475 | 4/1982 | Spalding | 198/429 |
| 4,417,935 | 11/1983 | Spencer | 156/80 |
| 4,543,141 | 9/1985 | Bradley | 156/164 |
| 4,650,173 | 3/1987 | Johnson | |
| 4,701,235 | 10/1987 | Craig | 156/519 |
| 4,711,683 | 11/1987 | Merkatoris | 156/164 |
| 4,945,252 | 7/1990 | Lerner et al. | 250/548 |

Primary Examiner—David A. Simmons
Assistant Examiner—Robert Barker
Attorney, Agent, or Firm—Tilton, Fallon, Lungmus & Chestnut

[57] ABSTRACT

Apparatus and method for cutoff register control for diaper machines wherein an advancing diaper web is sensed by strobe light imaging in connection with a point fixed in space to produce a distance value between the leading edge of the diaper pad and the fixed point, comparing the image distance with a predetermined value and then adjusting the means for cutoff and strobe trigger to bring the distance and picture within the value range.

7 Claims, 2 Drawing Sheets

APPARATUS AND METHOD FOR CUTOFF REGISTER CONTROL FOR DIAPER MACHINES

BACKGROUND AND SUMMARY OF INVENTION

This invention relates to apparatus and method for cutoff register control for diaper machines and, more particularly, to apparatus and method employing strobe light imaging prior to diaper cutoff.

Disposable diapers generally consist of an absorbent pad confined between a moisture impervious web (polyethylene) and a moisture pervious (non-woven)—see co-owned U.S. Pat. Nos. 4,417,935; 4,543,141; 4,701,239; and 4,711,683. These are made continuously by advancing one of the webs along a longitudinally extending path, applying the absorbent pad material and then applying the second web. The webs are usually longitudinally folded to provide a more compact product after which the webs are transversely severed between pads to provide diaper lengths of predetermined size.

There has been a problem in the precise location of the cutoff. Cutoff registration systems have long been in use. For example a scanner would sense the pad leading edge and a signal would be issued to advance or retard the position of the cutoff roll. However, this operation was not exact and it was felt that a video imaging system would make it possible to obtain a much improved measurement of the pad edge. One of the problems however, is that the "video snapshot" must be accurately timed to properly "frame" the diaper—in contrast to the previously employed registration scanner which looked continuously for the pad edge.

The typical method for registration using a video imaging system is to employ a scanner or other trigger device to time the picture and then analyze the image to measure the distance between features on the object. This has presented another problem in the case of diaper cutoff because there is no convenient view of the final diaper, the same having been folded before cutoff. Additionally, the elastic in the diaper causes the contract and change shape after cutoff so that image analysis is very difficult.

This invention describes a means and method for achieving the improved video sensing using a simple, practical means and method. More particularly, the invention controls the cutoff by strobe light imaging the leading pad edge and a point fixed in space prior to cutoff, comparing the imaged distance between the pad edge and the fixed point with a predetermined value range and thereafter adjusting the means for cutting and concurrently the strobe trigger point to bring the distance into the value range.

Now that the diaper picture is staying in the proper reference frame because the strobe timing adjusts to keep it there, the other registration measurement points for the diaper can be taken and all portions of the diaper can be registered to exact dimensions.

Now that the image of the diaper is always within the frame of the camera, registration of the fluff cutout, final cutout, foam placement, tab placement is achieved by using line measurements from the fixed reference point to each register point in the diaper. Each registration point is then motor controlled to bring the points into specified limits.

Other objects and advantages of the invention may be seen in the details of construction and operation set forth in the ensuing specification.

DESCRIPTION OF THE DRAWINGS

The invention is described in conjunction with an illustrative embodiment in the accompanying, in which—

DETAILED DESCRIPTION

Figure 1:
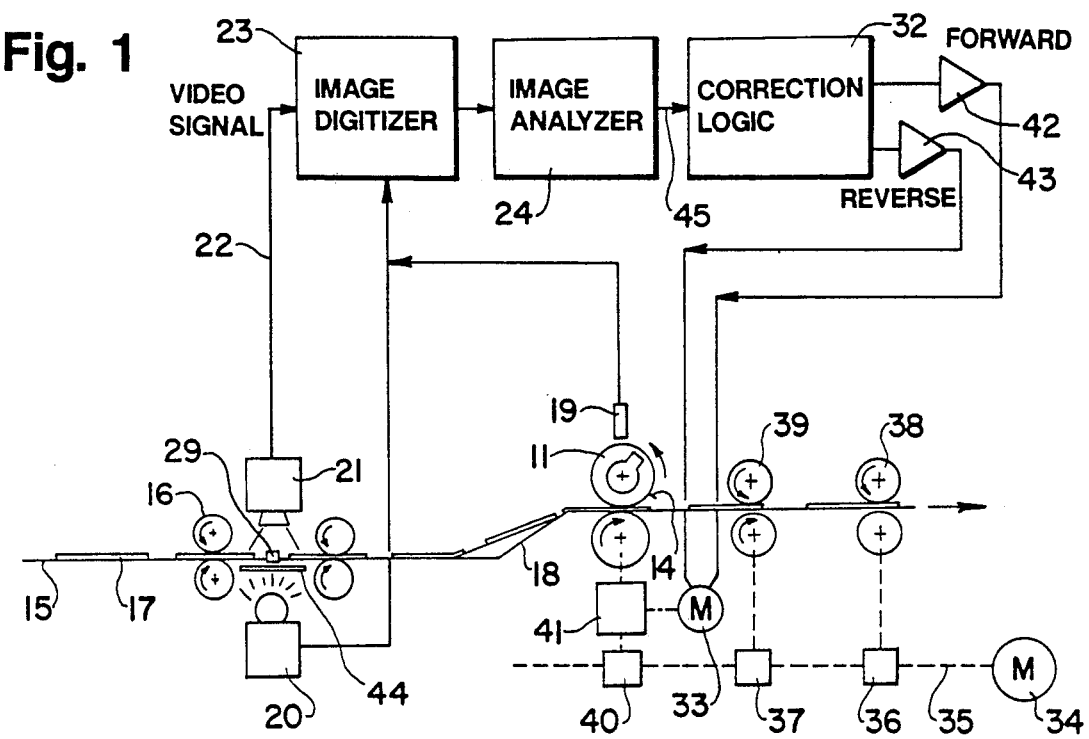
FIG. 1 is a side elevational view of diaper manufacturing apparatus.
Figure 2:
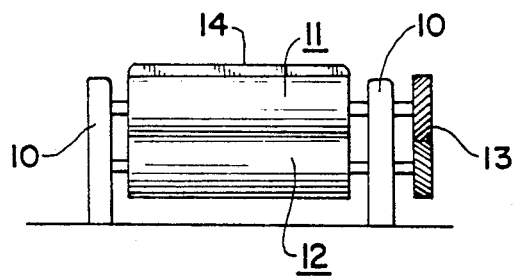
FIG. 2 is an end elevational view, also substantially schematic, of the diaper machine of FIG. 1.

With reference to the drawing and more particularly FIG. 2, the numeral 10 designates a pair of side frames which define a longitudinally extending path for the processing of diapers. Rotatably mounted on the side frames 10 are a pair of cutoff rolls 11 and 12 driven by gearing 13 with the cutoff roll 11 carrying a knife 14. The cutoff rolls 11 and 12 can be seen in the central portion of FIG. 1.

Now referring to FIG. 1, the diaper producing apparatus is illustrated schematically. At the extreme left, an underlying web 15 is shown being advanced along a longitudinally extending path by draw rolls 16. Omitted for clarity of presentation is the upper confining web. As indicated previously, sandwiched between the webs is an absorbent pad 17.

In accordance with conventional practice, the pad-equipped web is advanced into a folder 18 which longitudinally folds the side edges of the webs into overlying relation with the pad after which cutoff of the web occurs through the operation of the rolls 11, 12 to provide discrete diaper length after which the lengths are delivered to a stacker (not shown). Illustrative of stackers are co-owned U.S. Pat. Nos. 4,325,475 and 4,650,173.

Operation Generally

A strobe switch 19 — see the central portion of FIG. 1—is triggered once each revolution of the cutoff roll 11. This signals a strobe light 20 and an image is recorded by the camera 21 positioned on the other side of the web 15 from the strobe light 20. This develops a video signal which is delivered along the line 22 to an image digitizer 23 and an image analyzer 24 which compares the recorded image against a previously established value range.

Figure 3:
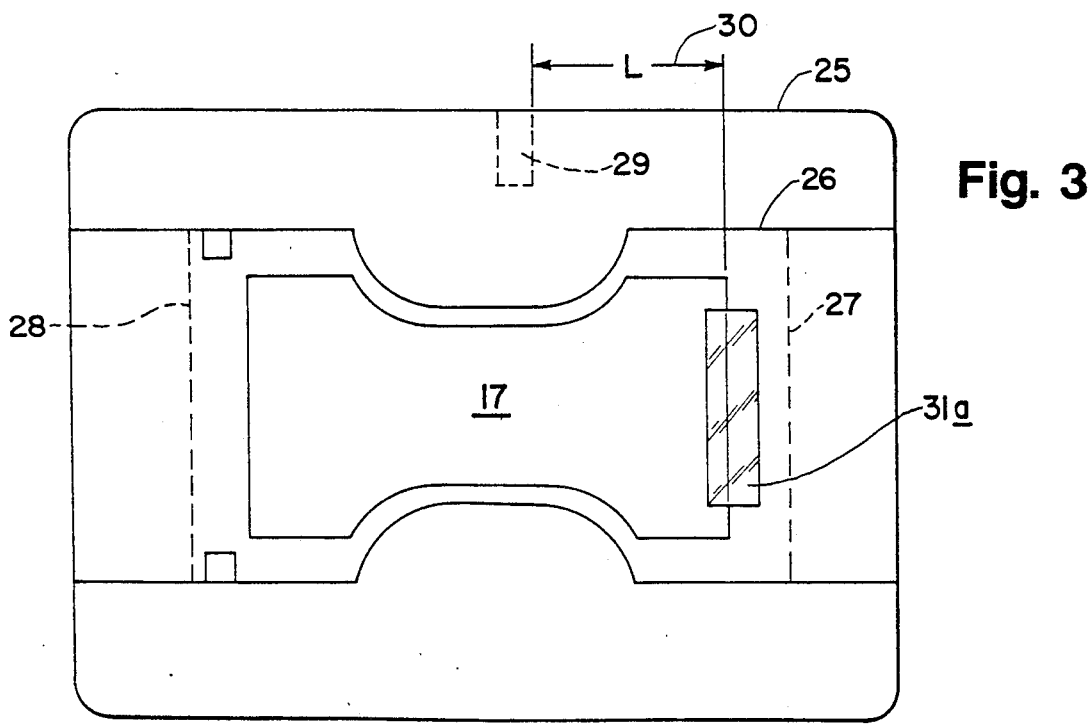
FIG. 3 is a top plan view of a top plan view of a portion of the diaper operation illustrating the aforesaid imaging.
Figure 4:
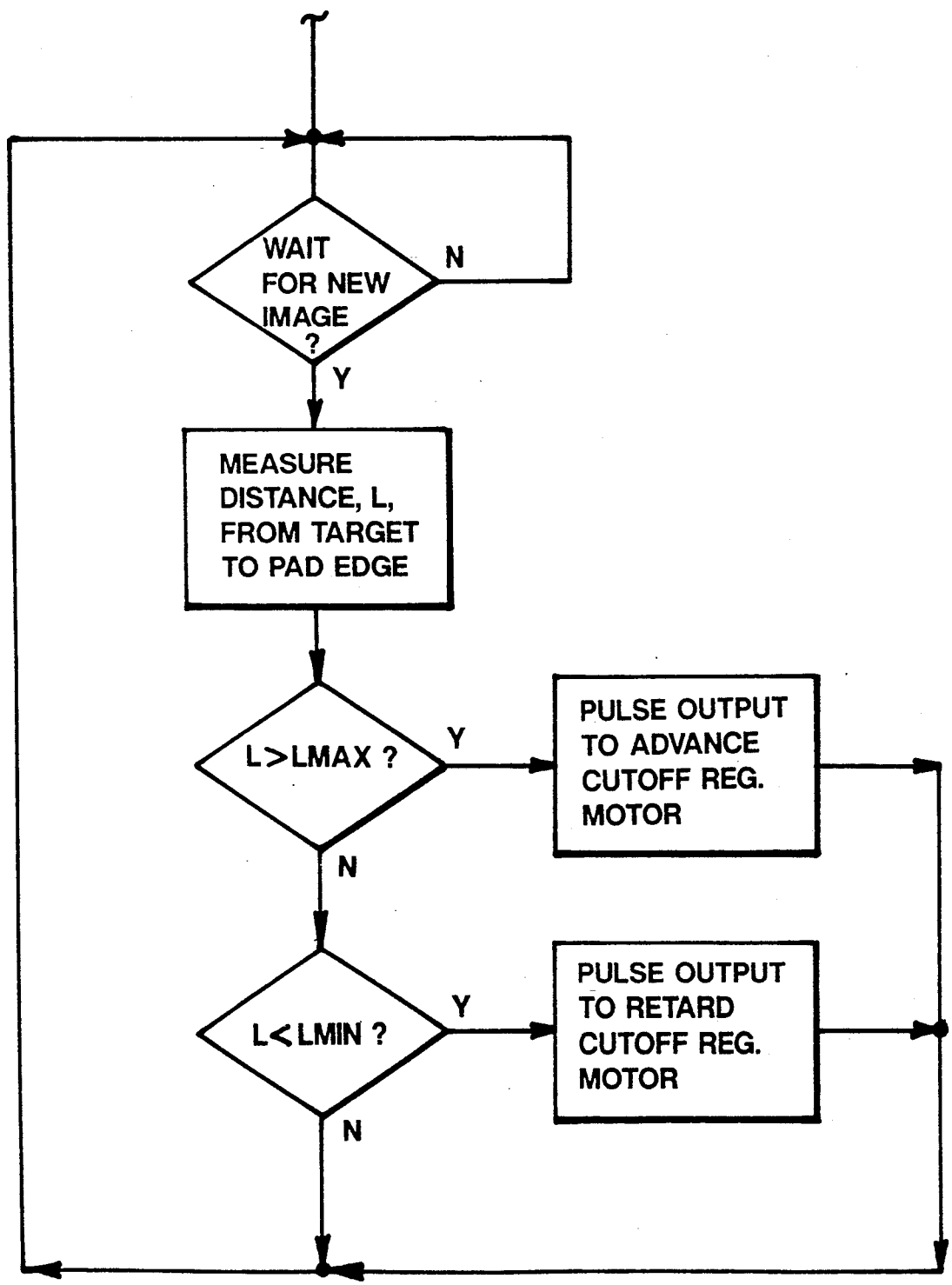
FIG. 4 is a schematic diagram of the correction logic employed in the practice of the invention.

For example and referring to FIG. 3, the closed outline 25 represents the camera field of view and it will be seen that this embraces one diaper length 26 between projected transverse lines of severance 27, 28. Provided on the machine frame is a point fixed in space, i.e., the target 29. This provides one end of a length measurement between the leading edge 31 of the pad 17 and the target 29. More particularly, the captured portion of the leading edge is the inspection window 31a. This recorded distance is compared with a predetermined value by virtue of the image digitizer and analyzer 23, 24 and correction logic as at 32 is employed to advance or retard the cutoff rolls 11 and 12 by virtue of a motor 33.

If the length 30 is within the preset range, no registration action is taken. If the length 30 is less than a preset minimum, then the correction motor is run for a short time to retard the cutoff rolls 11, 12. If the length is greater than the preset maximum, then the correction motor is run for a short time to advance the cutoff rolls.

In this manner, not only is the cutoff registration maintained, but the diaper is maintained in the same reference to the camera as registration corrections are made.

The target 29 on the machine frame can also be an imaginary target in the image frame. It is preferable, however, to use an actual target on the frame so that the registration accuracy is not subject to small camera vibrations or misalignments.

Drive Details

Referring again to FIG. 1, the numeral 34 designates the main drive motor for the diaper line and which is employed to turn a line shaft 35 coupled by gear boxes 36 and 37 to draw or pull rolls 38 and 39. The line shaft is also coupled by means of a gear box 40 to a differential 41 which is operated by the motor 33 in response to signals from the correction logic 32 delivered either to a forward signaling device 42 or a reverse signaling device 43 both of which are coupled to the motor 33.

Strobe System Details

Employed in connection with the strobe 20 is a diffuser plate 44 and also designated on FIG. 1 is the target 29. The camera 21 records an image which, as pointed out previously, is delivered as a video signal along line 22 to comparing means such as the image digitizer and image analyzer. These are currently available from VIDEK a KOKAK company of Canandaigua, New York 14425-9597 as Model RM-1000. The VIDEK RM-1000 vision system is designed to solve measurement and inspection problems using edge measurement and gray scale histogram window analysis techniques.

After the image has been analyzed and the output delivered to line 45, correction logic embodying the preset minimum and maximum values delivers and output signal either to motor drive outputs 42 (forward) or 43 (reverse).

Through the operation of the invention, the location or position of the cutoff is much more precise than that heretofore available and the problems of comparison with the folded, elasticized product are avoided.

The inventive vision concept may be used to analyze any part of the product with respect to a known target and then make registration adjustments accordingly. Thus, the invention is applicable to operations other than cutoff; i.e., the strobe signal could be initiated by the waistband applicator instead of the cutoff knife to regulate the waistband position.

While in the foregoing specification a detailed description of an embodiment of the invention has been set down for the purpose of illustration, many variations in the details hereingiven may be made by those skilled in the art without departing from the spirit and scope of the invention.

I claim:

1. Apparatus for cutoff register control for diaper machines comprising a frame,
   means for advancing a continuous diaper web along a longitudinally extending path, said web being equipped with longitudinally spaced apart absorbent pads,
   strobe light means on said frame in said path, cutoff means on said frame downstream of said strobe light means for transversely severing said web between adjacent pads,
   strobe light signal means coupling said cutoff means to said strobe light means for actuating said strobe light means as a function of the operation of said cutoff means,
   camera means operably associated with said strobe light means to record an image of a diaper pad and a fixed point on said frame,
   means for comparing the distance between the edge of an imaged pad and said fixed point with a predetermined acceptance distance range, and
   means for changing the operation of said cutoff means whenever the recorded distance is outside said range to bring the distance in a following pad within said range.

2. The apparatus of claim 1 in which said comparing means includes image analyzing means and computer means coupled between said camera means and said operation changing means.

3. The apparatus of claim 1 in which said cutoff means includes knife-equipped roll means rotatably mounted on said frame to cyclically cut said web, means operably associated with said frame for rotating said roll, said strobe light signal means being responsive to the cyclic cutting of said web.

4. The apparatus of claim 3 in which said operation changing means includes motor means to advance or retard the rotating of said roll means.

5. The apparatus of claim 1 in which said frame is equipped with means for longitudinally folding said web about said pad, said folding means being positioned in said path between said strobe light means and said cutoff means.

6. In a method for controlling the cutoff in a diaper machine, the steps of:
   advancing a diaper web along a longitudinally extending path with said web being equipped with longitudinally spaced apart absorbent pads,
   transversely severing said web between pads at a predetermined position in said path,
   strobe light imaging the leading pad edge and a point fixed in space, said imaging occurring at an area upstream of said severing position,
   comparing the imaged distance between said pad edge and fixed point with a predetermined value range, and
   adjusting said severing means to bring said distance into said value range.

7. The method of claim 6 in which said severing step includes rotating a pair of cutoff rolls, said imaging step being correlated to the roll rotation and said adjusting step including altering the speed of rotation of said rolls.

* * * * *